US012357759B2

(12) United States Patent
Powers et al.

(10) Patent No.: US 12,357,759 B2
(45) Date of Patent: Jul. 15, 2025

(54) MEDICAL INJECTOR, SYRINGE, AND CONNECTOR

(71) Applicant: Espire-Medical, LLC, Chesterfield, MO (US)

(72) Inventors: John Edward Powers, Wildwood, MO (US); Thomas D. Winkler, Fenton, MO (US); David L Wojcicki, Dittmer, MO (US)

(73) Assignee: Espire-Medical, LLC, Wildwood, MO (US)

( * ) Notice: Subject to any disclaimer, the term of this patent is extended or adjusted under 35 U.S.C. 154(b) by 1504 days.

(21) Appl. No.: 16/597,342

(22) Filed: Oct. 9, 2019

(65) Prior Publication Data

US 2020/0108197 A1 Apr. 9, 2020

Related U.S. Application Data

(60) Provisional application No. 62/743,174, filed on Oct. 9, 2018.

(51) Int. Cl.
| | | |
|---|---|---|
| *A61M 5/315* | (2006.01) | |
| *A61M 5/00* | (2006.01) | |
| *A61M 5/145* | (2006.01) | |
| *A61M 5/31* | (2006.01) | |

(52) U.S. Cl.
CPC ...... *A61M 5/31515* (2013.01); *A61M 5/1452* (2013.01); *A61M 5/1456* (2013.01); *A61M 5/3134* (2013.01); *A61M 5/31511* (2013.01); *A61M 5/31513* (2013.01); *A61M 5/007* (2013.01); *A61M 2205/33* (2013.01)

(58) Field of Classification Search
CPC .. A61M 5/007; A61M 5/1452; A61M 5/1456; A61M 5/3134; A61M 5/31511; A61M 5/31513; A61M 2205/33; A61M 5/31515
See application file for complete search history.

(56) References Cited

U.S. PATENT DOCUMENTS

| | | | | |
|---|---|---|---|---|
| 5,090,962 A | * | 2/1992 | Landry, Jr. | ......... A61M 5/31511 604/110 |
| 5,181,912 A | * | 1/1993 | Hammett | ............ A61M 5/5066 604/110 |
| 5,352,202 A | * | 10/1994 | Hammett | ............ A61M 5/3216 604/110 |
| 6,339,718 B1 | | 1/2002 | Zatezalo | |

(Continued)

*Primary Examiner* — James D Ponton
(74) *Attorney, Agent, or Firm* — David E. Crawford; Crawford I.P. Law (57) ABSTRACT

A syringe including a barrel having an interior surface defining an interior extending along a longitudinal axis between an open end and a closed end opposite the open end. The closed end has an orifice that opens to a nozzle extending from the closed end. The syringe includes a plunger including a support and a seal attached to the support. The seal defines a selectively variable volume hollow cavity within the interior of the barrel. A receiver extends longitudinally from a connector face of the support. The receiver includes multiple jaws spaced for receiving an injector fastener having an insertion end and a retention land. Each jaw has an elastically deformable arm and a catching surface for engaging a retention land of the injector fastener when the injector fastener is seated between the jaws.

13 Claims, 14 Drawing Sheets

(56) References Cited

U.S. PATENT DOCUMENTS

| | | | |
|---|---|---|---|
| 6,520,930 | B2 | 2/2003 | Critchlow |
| 6,643,537 | B1 | 11/2003 | Zatezalo |
| 6,652,489 | B2 | 11/2003 | Trocki |
| 6,673,033 | B1 | 1/2004 | Sciulli |
| 6,733,477 | B2 | 5/2004 | Cowan |
| 6,958,053 | B1 | 10/2005 | Reilly |
| 7,018,363 | B2 | 3/2006 | Cowan |
| 7,029,459 | B2 | 4/2006 | Reilly |
| 7,079,886 | B2 | 7/2006 | Zatezalo |
| 7,419,478 | B1 | 9/2008 | Reilly |
| 7,462,166 | B2 | 12/2008 | Cowan |
| 7,465,290 | B2 | 12/2008 | Reilly |
| 7,497,843 | B1 | 3/2009 | Castillo |
| 7,540,856 | B2 | 6/2009 | Hitchins |
| 7,553,294 | B2 | 6/2009 | Lazzaro |
| 7,666,169 | B2 | 2/2010 | Cowan |
| 7,682,345 | B2 | 3/2010 | Savage |
| 7,691,085 | B2 | 4/2010 | Dedig |
| 8,133,203 | B2 | 3/2012 | Hack |
| 8,307,693 | B2 | 11/2012 | Uram |
| 8,439,876 | B2 | 5/2013 | Spohn |
| 8,574,200 | B2 | 11/2013 | Hack |
| 8,721,596 | B2 | 5/2014 | Trocki |
| 8,821,450 | B2 | 9/2014 | Cowan |
| 8,926,569 | B2 | 1/2015 | Bisegna |
| 9,314,565 | B2 | 4/2016 | Spohn |
| 9,636,452 | B2 | 5/2017 | Trocki |
| 9,694,131 | B2 | 7/2017 | Cowan |
| 9,844,622 | B2 | 12/2017 | Savage |
| 9,855,390 | B2 | 1/2018 | Bisegna |

* cited by examiner

MEDICAL INJECTOR, SYRINGE, AND CONNECTOR

BACKGROUND

The present disclosure generally relates to syringes, and, more particularly, to a medical injector syringe and connector.

Medical injectors are used to inject fluids such as contrast media into patients for imaging biological structures. Many conventional injectors use specialized syringes, particularly configured for use with the specific medical injector type. Because the syringes are specialized, manufacturing cost for the syringes is substantially higher than conventional medical syringes. These specialized syringes typically include both uniquely adapted barrels and uniquely adapted plungers. Frequently, the injectors are inoperable when use with a syringe other than the specialized syringe is attempted. In some instances, the additional cost may provide advantages such as providing syringe encoding for verifying whether the syringe is properly positioned in the injector or whether the syringe is empty. Many of these advantages can be accomplished without requiring specialized syringes. In some instances, the advantages are unnecessary or rarely used.

Manufacturers of conventional medical injectors pass the cost of the specialized syringes on to health care providers, increasing the cost of medical care. The manufacturers or their licensees may be the only available source for the syringes, minimizing or eliminating competition and allowing higher pricing. Although manufacturers benefit from higher pricing, the benefit comes at the expense of healthcare consumers. Therefore, there is a need for a medical injector syringe and connector system having a reduced manufacturing cost.

SUMMARY OF THE DESCRIPTION

In one aspect, the description includes a syringe, comprising a tubular syringe barrel having an interior surface defining an interior of the barrel extending along a longitudinal axis between an open end and a closed end opposite the open end. The closed end has an orifice that opens to a nozzle that extends from the closed end of the syringe barrel opposite the hollow interior. Further, the syringe includes a syringe plunger, comprising a support having a seal face and a connector face opposite the seal face. A seal is attached to the seal face of the support. The seal is sized and shaped for sealing slidable engagement with the interior surface of the syringe barrel. The seal defines a selectively variable volume hollow cavity within the interior of the syringe barrel between the seal and the closed end of the syringe barrel. A receiver extends longitudinally from the connector face of the support. The receiver comprising a plurality of jaws spaced for receiving an injector fastener having an insertion end and a retention land spaced from the insertion end. Each jaw has an elastically deformable arm and a catching surface spaced from the connector face for engaging the retention land of the injector fastener when the injector fastener is seated between the jaws.

In another aspect, the description includes a method of adapting a syringe plunger for use in combination with an injector fastener having an insertion end and a retainer spaced from the insertion end. The plunger includes a disk-shaped support, a seal attached to a first face of the support, and a stem extending from a second face of the support to a head. The stem has a cross section including two pairs of elongate blades extending radially outward from a common axis to an outer edge. Each blade of the pair is coplanar with the other blade of the pair of blades. Each pair of blades is perpendicular to the other pair of blades. The method comprises partitioning a first pair of plunger stem blades to a predetermined configuration. The plunger is rotated ninety degrees about the common axis of the pairs of blades and a second pair of plunger stem blades is partitioned to the predetermined configuration. The stem is separated along cuts formed during the partitioning steps to form an adapted plunger having a receiver comprising a plurality of jaws spaced for receiving the injector fastener.

In yet another aspect, the description includes a connector, comprising a fastener having an insertion end and a retention land spaced from the insertion end. The connector also includes a plurality of jaws extending from a common body. The plurality of jaws is spaced for receiving the fastener. Each jaw of the plurality of jaws has an elastically deformable stem and a catch spaced from the body for engaging the retention land of the injector fastener when the fastener is seated between the jaws of the receiver, providing a particular geometry adapted to automatically join and release the connector from the receiver.

In still another aspect, the description includes an injector, comprising a syringe receiver having at least three cylindrical ports. Each port is sized and shaped for receiving a barrel of a syringe having a longitudinal axis and a plunger reciprocably received in the barrel for movement along the longitudinal axis. The injector also includes an actuator positionable for moving parallel to the longitudinal axis of at least one syringe when the syringe is received within a port. In addition, the injector has a connector mounted on the actuator for selectively joining the actuator to the syringe and a controller operatively connected to the actuator for controlling the actuator to drive the plunger of the syringe for movement along the longitudinal axis.

BRIEF DESCRIPTION OF THE DRAWINGS

Corresponding reference characters indicate corresponding parts throughout the drawings.

DETAILED DESCRIPTION OF THE DRAWINGS

Figure 1:
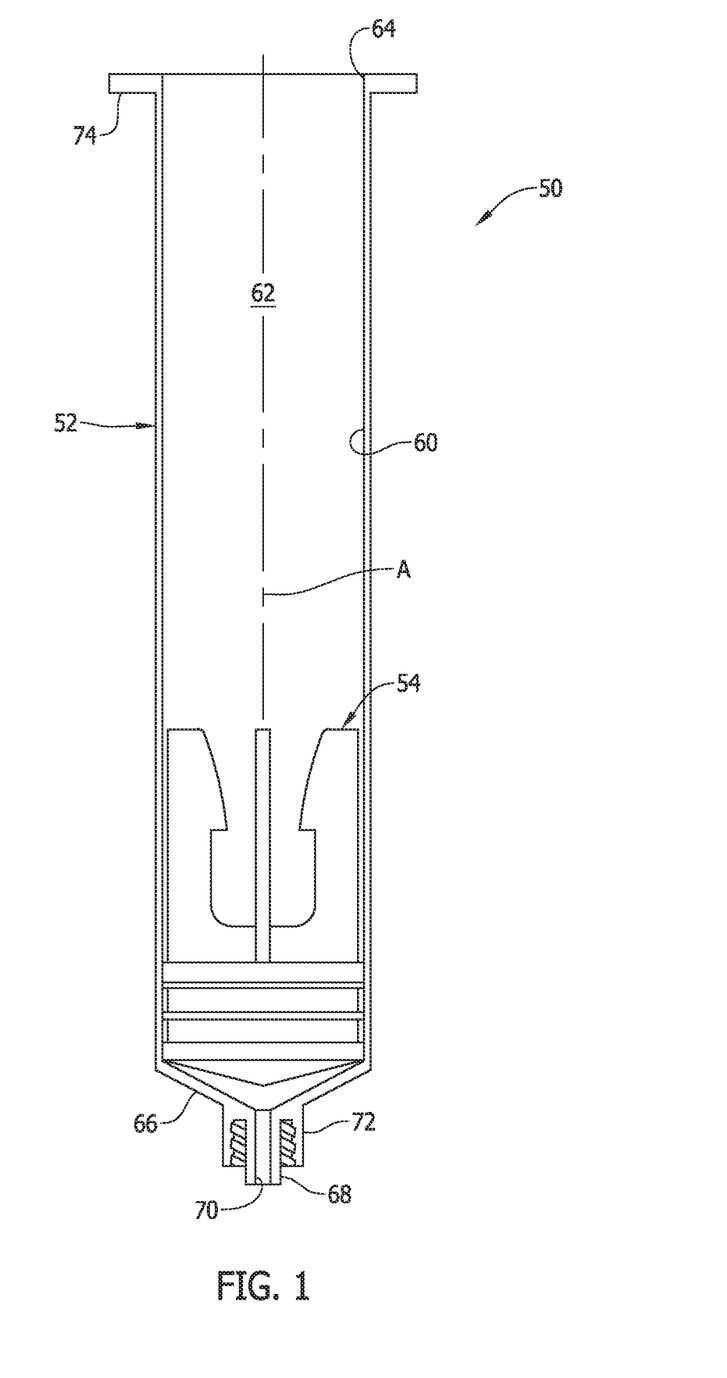
FIG. 1 is a front elevation of a syringe as described.

Referring to FIG. 1, a syringe is designated in its entirety by the reference number 50. The syringe 50 generally comprises a tubular cylindrical barrel (generally designated by 52) and a plunger (generally designated by 54). The barrel 52 has an interior surface 60 defining a hollow interior 62 extending along an imaginary central longitudinal axis designated by A. The barrel 52 has an open upper end 64 and a closed lower end 66 opposite the open end. A nozzle 68 having an orifice 70 and a Luer tip connector 72 is provided at the closed end 66 of the barrel 52, allowing fluid to be drawn into and expelled from the hollow interior 62 in a conventional manner. A flange 74 surrounds the open end 64 of the barrel 52. Other features of the barrel 52 are conventional, and will not be described in further detail. Although the barrel may be made of other materials, in the illustrated example the barrel is made from polypropylene.

Figure 2:
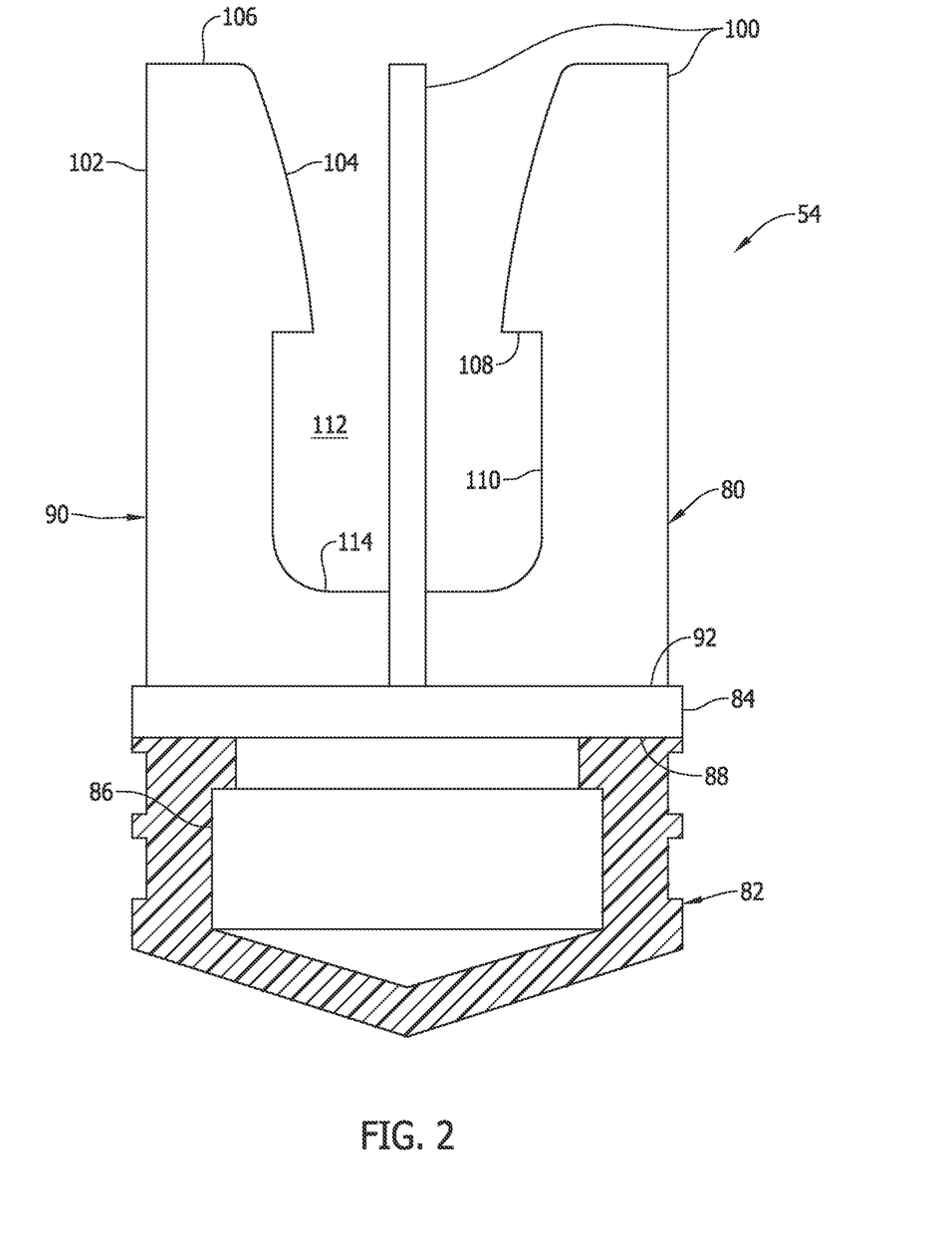
FIG. 2 is a vertical cross section of a plunger of the syringe.

As illustrated in FIG. 2, the syringe plunger 54 comprises a support, generally designated by 80, and a seal, generally designated by 82. The support 80 includes a circular disk 84 having a button 86 extending downward from a lower seal face 88 and receiver, generally designated by 90, extending upward from an upper connector face 92. The plunger seal 90 is attached to the button 86 of the support 80. The seal 82 is sized and shaped for sealing slidable engagement with the interior surface 60 of the syringe barrel 52. Those skilled in the art will appreciate that the seal 82 forms an upper boundary of a cavity formed in the interior of the syringe barrel 52 having a selectively variable volume. The cavity extends to the closed end 66 and is surrounded by the interior surface 60 of the barrel 52 below the seal 82. As the seal 82 moves away from the closed end 66 (upward as shown), the volume of the cavity increases, and as the seal moves toward the closed end (downward), the volume of the cavity decreases. Other features of the seal 82 are conventional and will not be described in further detail. Although the seal may be made of other materials, in the illustrated example the seal 82 is made from a thermoplastic elastomer.

As further shown in FIG. 2, the receiver 90 includes cooperating pairs of hooked blades 100 forming opposing jaws. Each blade 100 includes a head 102 having a curved, sloped inner surface 104 for guiding a connector 160 (FIG. 5) between the jaws as will be explained. The sloped surface 104 extends between a terminal end 106 of each blade 100 and a catching surface 108 extending perpendicular to the longitudinal axis A (FIG. 1). In the illustrated example, each blade 100 has a thickness measured circumferentially of about 0.07 inches. Each illustrated blade 100 has a length measured longitudinally between the terminal end 106, and the connector face 92 of the disk 84 of about 1.20 inches. A narrower elastically deformable arm 110 adjacent the catching surface 108 allows the blade 100 to twist and bend when receiving or releasing a connector 160 (FIG. 5) as will be described below with reference to FIGS. 5-11. Each arm 110 of the illustrated example has a width measured in a radial direction of the disk 84 of about 0.22 inches. A socket or receptacle 112 is formed between the arms 110 of each pair of blades 100 for receiving a fastener of the connector as will be described below. A broad base 114 is provided between each arm 106 and the disk 84. The base 114 strengthen the disk 84 to prevent the disk from deflecting as the arms deform. In the illustrated example, the receiver 90 has two pairs of opposing jaws each formed by two blades 100. Receivers having other numbers of blades are envisioned. Although the receiver may be made of other materials, in the illustrated example the receiver 90 is made from polyethylene or polypropylene.

Figure 3:
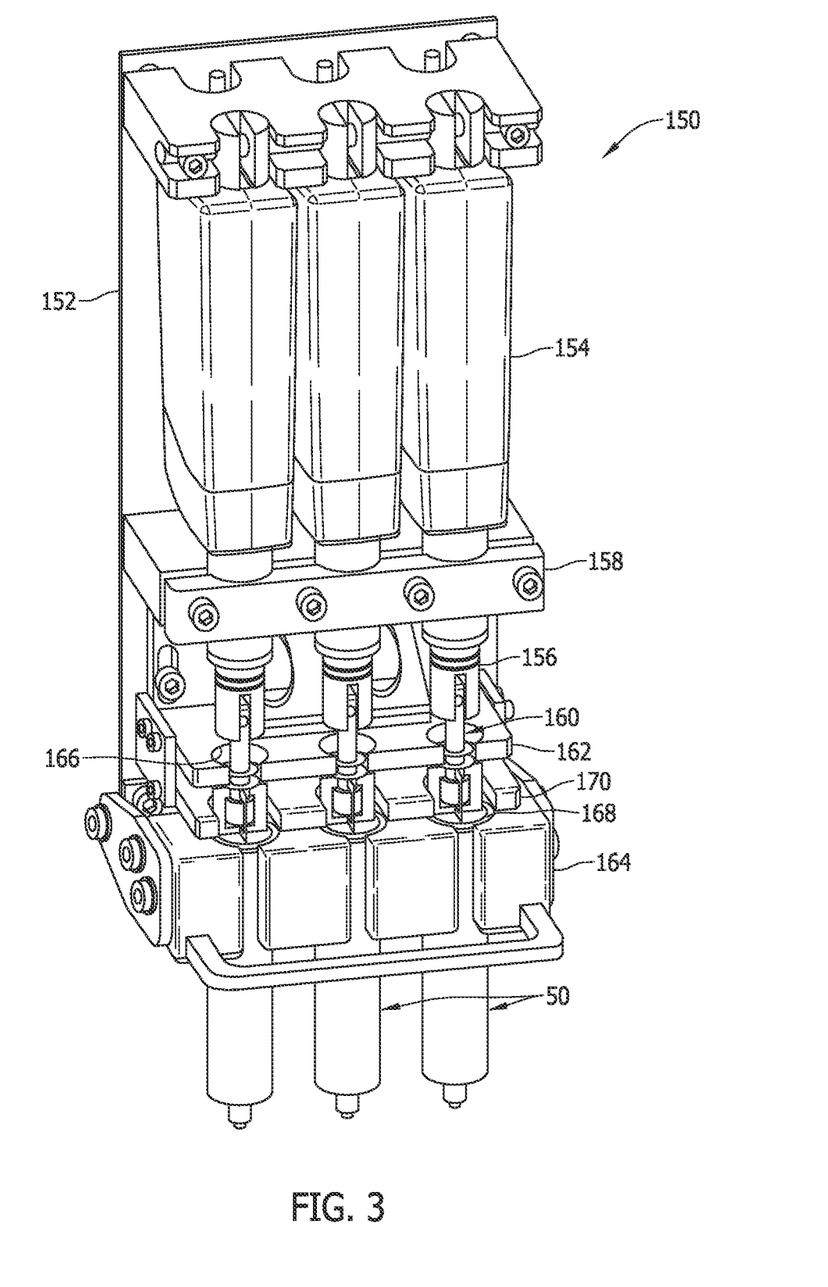
FIG. 3 is a perspective of a medical injector using syringes as described.
Figure 4:
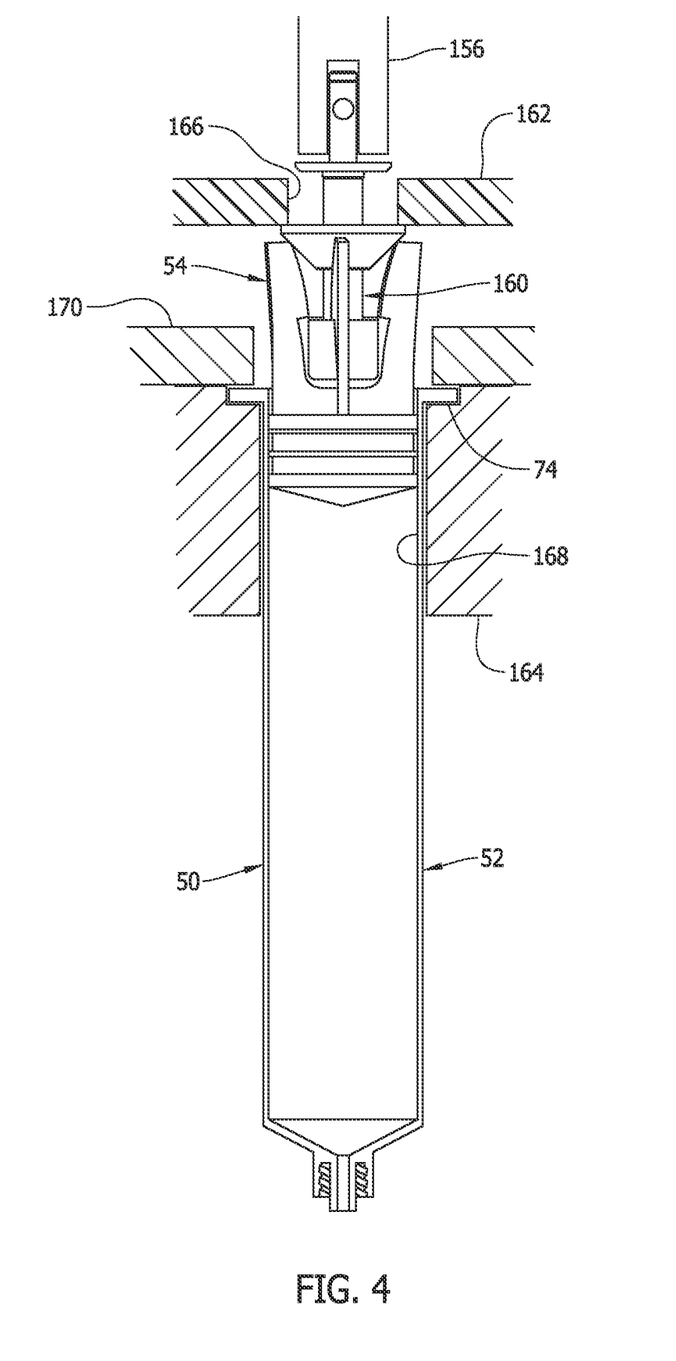
FIG. 4 is a front elevation of a connector of the medical injector system.
Figure 10:
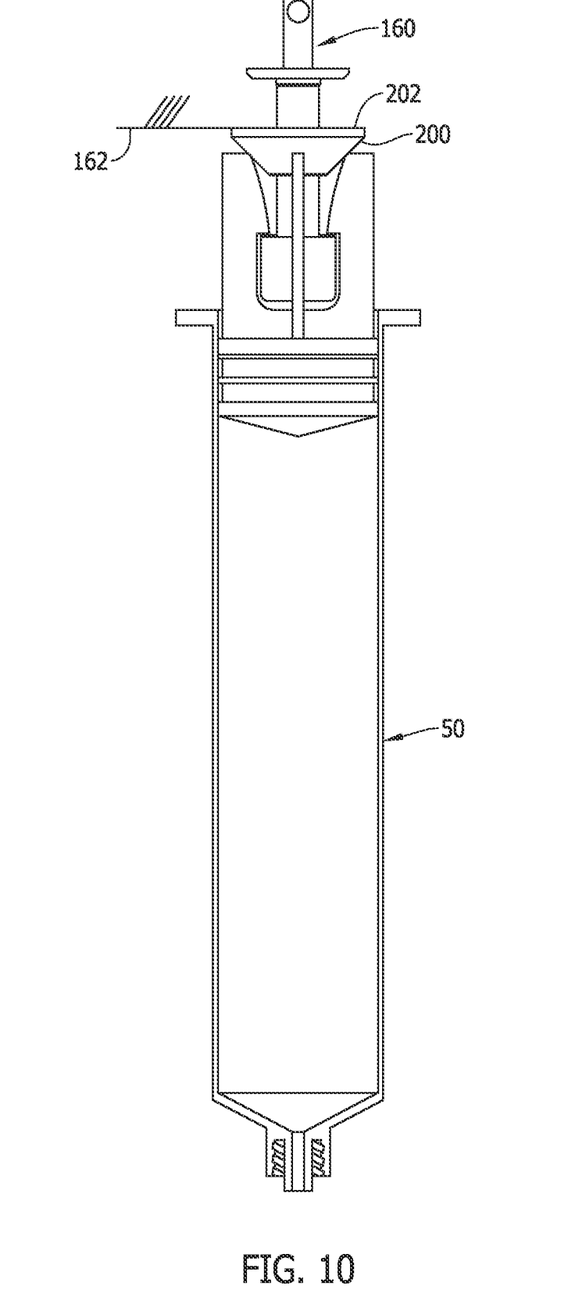
FIG. 10 is a front elevation of the syringe and the connector showing the connector contacting a stop of the system illustrated schematically.

FIG. 3 shows a medical injector, generally designated by 150, in which one or more syringes 50 as described above are installed to inject fluids, such as contrast media, into a patient for imaging biological structures. The injector 150 includes a mount 152 for receiving linear actuators 154. Each actuator 154 has a rod 156 that extends or retracts depending upon a signal received from a control unit (not shown). Although other actuators may be used, the illustrated actuators are WhisperTrak linear actuators available from Thomson Industries, Inc. of Marengo, Illinois, and Radford, Virginia. In the illustrated example, a clamp 158 provided on the mount 152 clamps the lower end of each actuator 150 to the mount and the upper end of each actuator is pivotally connected to the mount 152. A connector, generally designated by 160, is pivotably fastened to a lower end of the rod 156. The actuator 154 drives the connector 160 downward as the rod 156 extends from the actuator 154 and pulls the connector upward as the rod retracts. A stop 162 and a syringe receiver 164 extend from the mount 152 generally below the actuators 154. As illustrated in FIG. 4, the stop 162 includes a series of openings 166 permitting the rod 156 of the actuators 154 to extend through the stop. The openings 166 are sized to engage a portion of the connectors 160 when disconnecting the connector from the corresponding syringe plunger as will be described below with respect to FIG. 10. The syringe receiver 164 includes cylindrical ports 168, each of which is sized for receiving the barrel 52 of a corresponding syringe 50 to hold the syringe in alignment with the connector 160. Each port 168 is counterbored for receiving the flange 74 surrounding the open end 64 of the barrel 52. The receiver 164 is selectively pivotable downward to expose the ports 168 for inserting and removing syringes from the ports 168. Once the syringes 50 are inserted, the receiver 164 is pivoted upward to the position shown in FIGS. 3 and 4 so the receiver 164 is positioned below a clamping plate 170 extending from the mount 152 to retain the syringes in position in the receiver. A catch (not shown) holds the receiver 164 in the closed position with the connectors 160 and syringes aligned as shown in FIGS. 3 and 4. Although the illustrated injector 150 includes three actuators 154 and accommodates three syringes 50, injectors having other numbers of actuators and accommodating other numbers of syringes are envisioned. Further, the mount 154, stop 162, and clamping plate 170 of the illustrated example are formed from aluminum plate, but other materials are envisioned.

Figure 5:
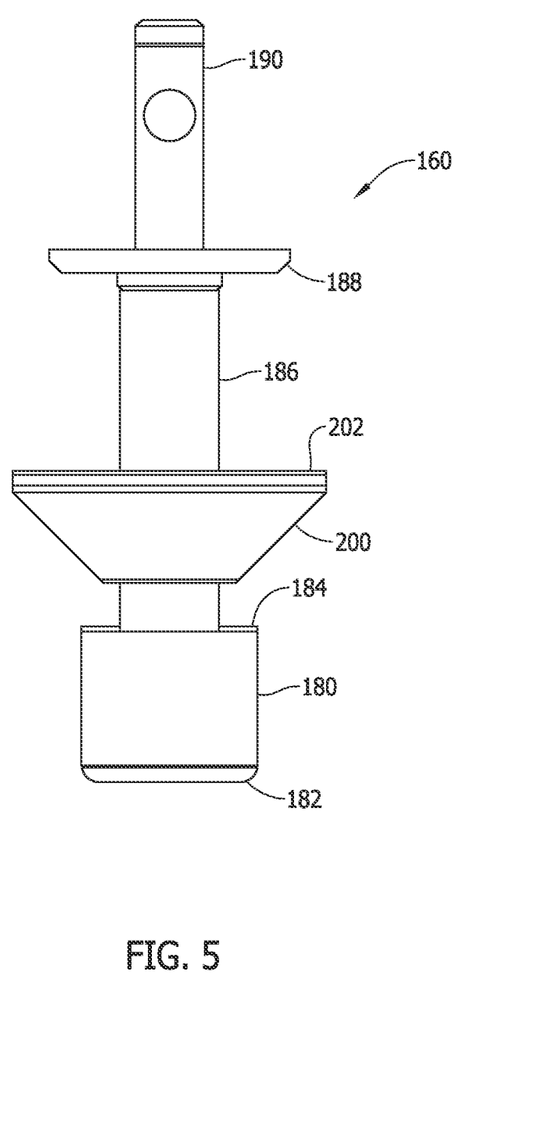
FIG. 5 is a fragmentary vertical cross sectional of the medical injector system holding a syringe.

As illustrated in FIG. 5, the connector 160 includes a cylindrical fastener element or fastener 180 having a rounded lower insertion end 182 and an annular planar upper retention land 184 spaced from the insertion end. A shaft 186 extends upward from the fastener 180 to a collar 188. A tongue 190 extending upward from the collar 188, is adapted to connect the connector 160 to the rod 156 of the actuator 154. The tongue 190 is received in a clevis 192 formed on the lower end of the rod 156 and pinned in place, providing a pivoting connection for aligning the connector 160 with the syringe. Although the illustrated example has a clevis connection, other connector types may be used. A conical spreader 200 is positioned on the connector shaft 186 for sliding movement upward and downward along the shaft between the fastener element 180 and the collar 188. The conical spreader 200 includes a planar upper face 202 for engaging the stop 162 of the injector 150. The face 202 has a diameter greater than the openings 166 in the stop to prevent the spreader 200 from passing through the openings as the actuator 154 raises the connector 160. In the illustrated example, the spreader 200 forms an angle of about 45 degrees with the longitudinal axis A (FIG. 1). Although the connector may be made of other materials, in the illustrated example the connector 200 is made from stainless steel.

Figure 6:
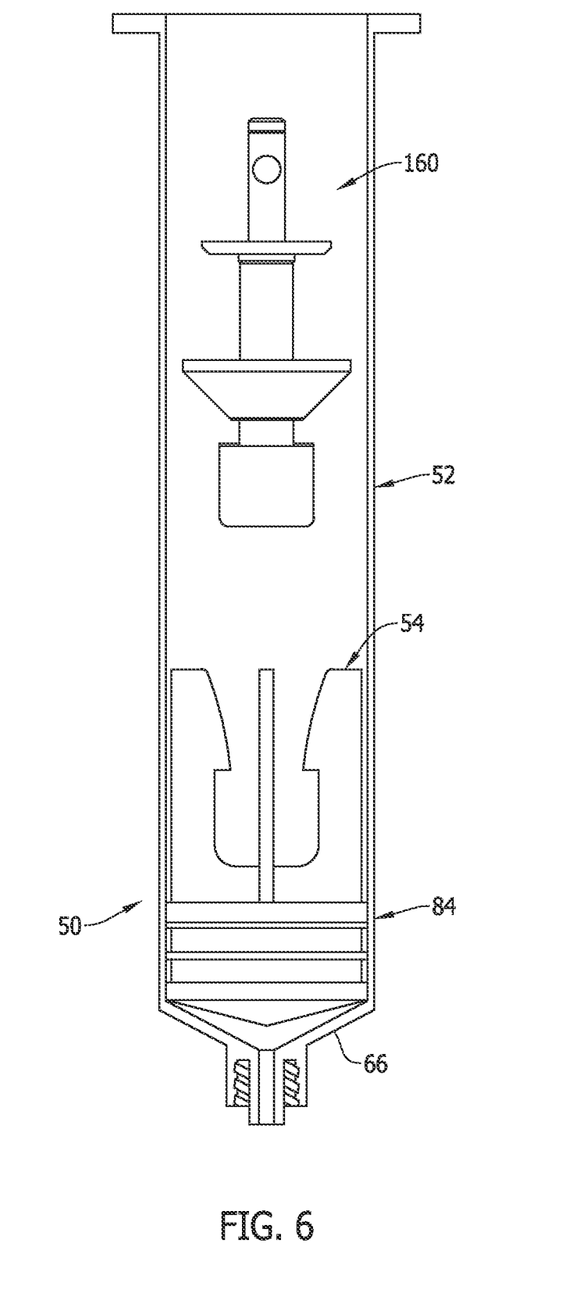
FIG. 6 is a front elevation of the syringe in section and the connector when the connector is lowered into the syringe.
Figure 7:
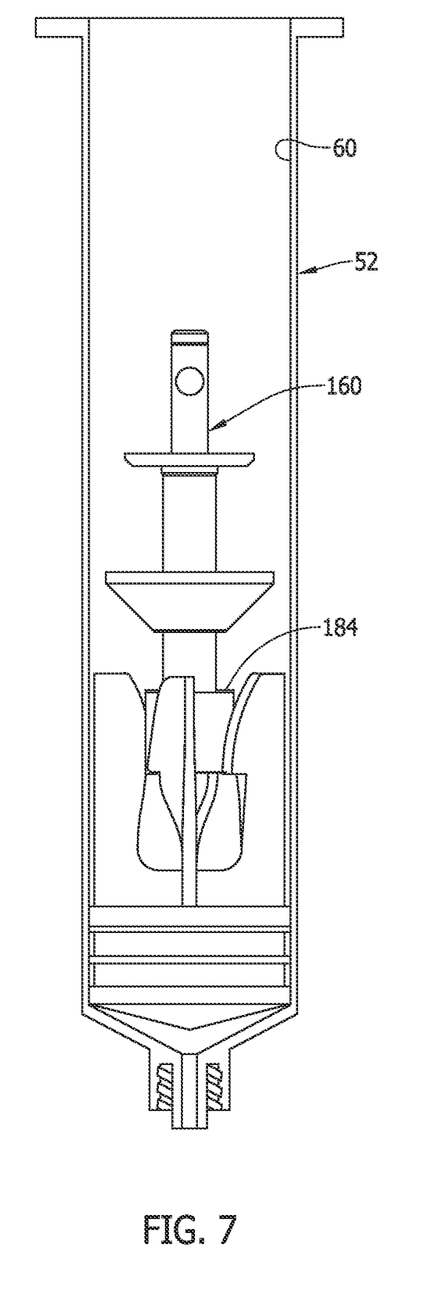
FIG. 7 is a front elevation of the syringe and the connector showing the connector deflecting the plunger blades.
Figure 8:
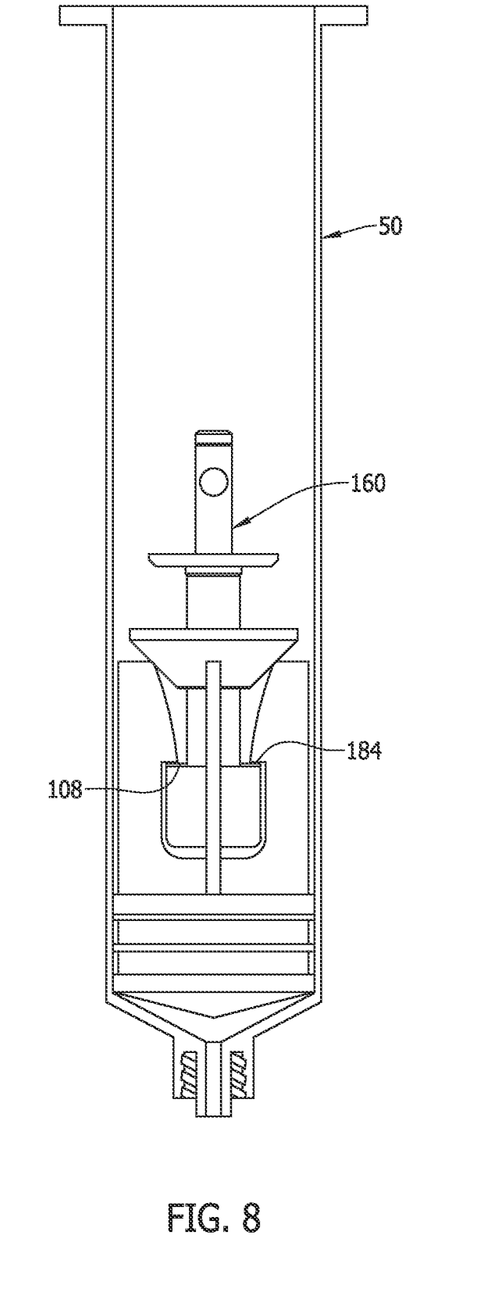
FIG. 8 is a front elevation of the syringe and the connector showing the connector joined with the syringe.
Figure 9:
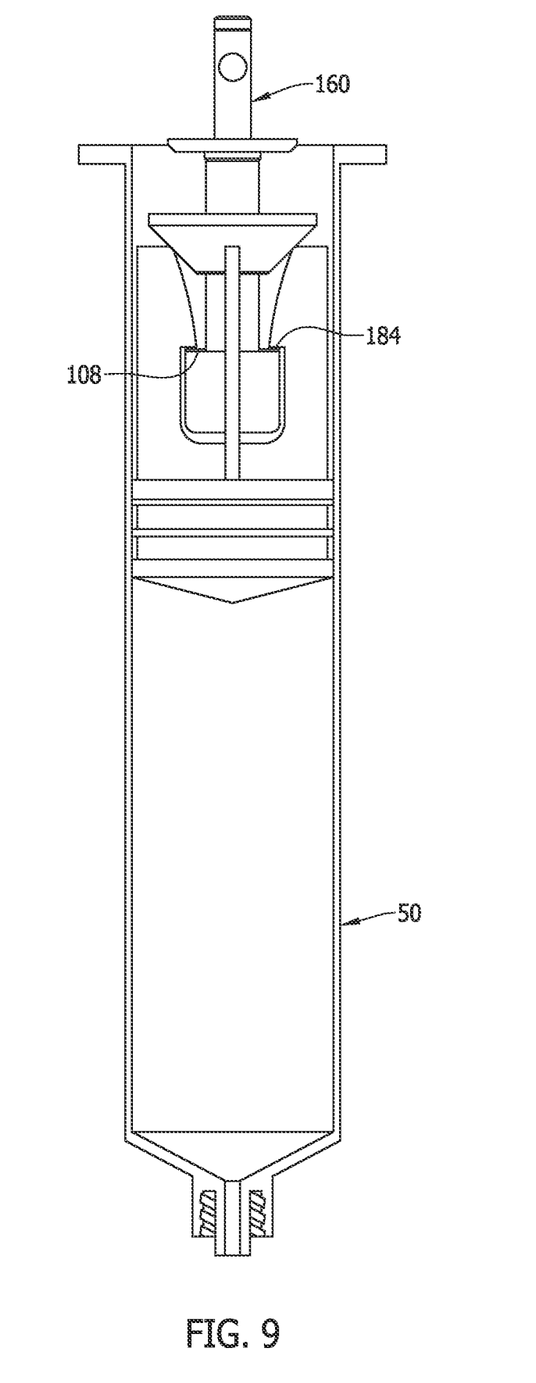
FIG. 9 is a front elevation of the syringe and the connector showing the connector raised to pull the plunger upward.

With reference to FIGS. 6-11, the connector 160 and syringe plunger 54 are adapted to automatically join when the actuator 154 pushes the connector downward against the plunger and to automatically release as the actuator pulls the connector upward. Although it is envisioned that the syringe may be filled with fluid prior to being loaded into the injector under some circumstances or protocols, the syringe 50 of the illustrated example is empty when loaded into the injector 150 and the plunger is positioned so the plunger seal 84 is seated against the closed end 66 of the syringe barrel 52 as shown in FIG. 6. The actuator 154 lowers the connector 160 into the barrel 52 of the syringe 50 in alignment with the central longitudinal axis A of the syringe. When the fastener 180 of the connector 160 engages the jaws of the plunger 54, the blades 100 deflect outward until the blades contact the inner surface 60 of the barrel 52 and then twist as shown in FIG. 7 to allow the fastener to pass between the jaws. As the actuator pushes the connector farther downward, the retention land 184 of the fastener passes the catching surfaces 108 of the blades and enters the receptacle 112. The resilient blades return to their undeflected shapes, so the catching surface 108 of each blade overlies the retention land 184. In this configuration, which is shown in FIG. 9, the connector 160 is joined to the plunger 54, so the plunger is drawn upward as the actuator 154 pulls the connector upward. The overlap between the catching surface 108 and retention land 184 is sufficient to prevent the jaws from releasing the fastener 180 even should the blades 100 deflect a minimal amount.

As the actuator 154 pulls the connector 160 farther upward, the engaging face 202 of the spreader 200 eventually engages the stop 162 (illustrated schematically in FIGS. 10 and 11), preventing the spreader from moving farther upward. When the actuator 154 pulls the connector 160 farther upward after the engaging surface 202 contacts the stop 162, the spreader 200 deflects the arms 110 outward. Because the blades 100 are outside the barrel 52 of the syringe 50, the arms 110 are free to deflect sufficiently to allow the fastener 180 to pass between the jaws to release the connector 160 from the receiver 164. Comparing FIG. 7 to FIG. 11, the arms 110 of the blades 100 twist more when the connector 160 is joining the plunger 54 than when the jaws of the plunger release the connector. Further, the arms 110 of the blades 100 deflect radially outward more when the plunger 54 is releasing the connector 160.

Figure 12:
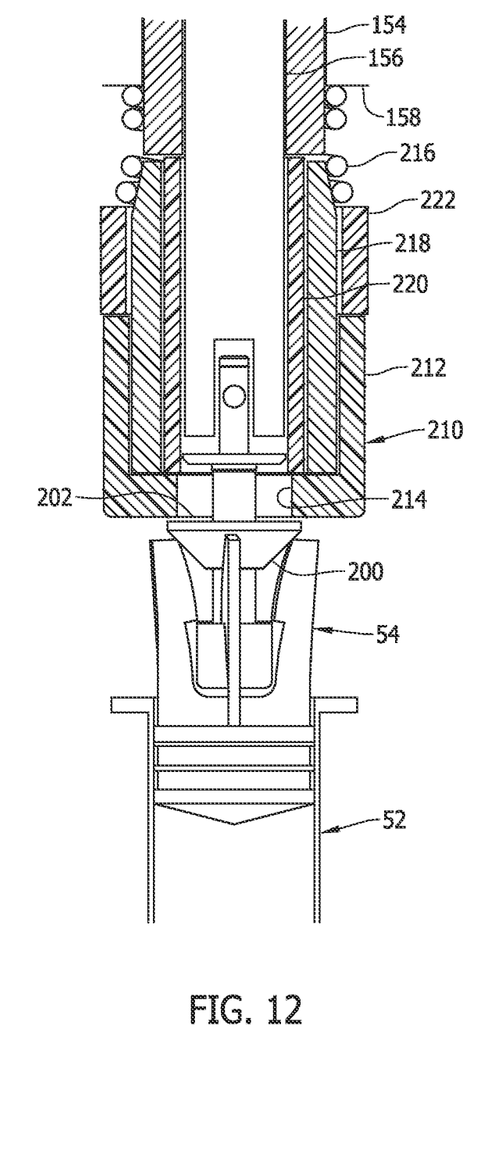
FIG. 12 is a fragmentary front elevation of the syringe and the connector showing an alternative spring-biased spreader stop.

FIG. 12 illustrates an alternative spring-biased spreader stop, generally designated by 210, which is used instead of the stop 162 described above. Each stop 210 includes a head 212 having an opening 214 sized to receive the shaft 186 of a connector 160 and prevent the spreader 200 from passing.

A coil spring 216 surrounding the actuator rod 156 between the head 212 and the actuator clamp 158 biases the head downward and away from the actuator rod. As the rod 156 pulls the connector 160 upward, the engaging surface 202 of the spreader 200 contacts the head 212, pushing the spreader downward against the jaws of the plunger 54. When the rod 156 is sufficiently retracted, concentric tubes 218, 220 surrounding the actuator rod 156 between the actuator 154 and the head 212 engage the head to prevent the head from moving farther upward. When the actuator 154 pulls the connector 160 farther upward after the engaging surface 202 contacts the head 212, the spreader 200 deflects the arms 110 outward as described above. A collar 222 surrounding the tubes 218, 220 above the head 212 is positioned between the spring 216 and the head. As will be appreciated by those skilled in the art, the spring 216 and the collar 222 are sized to ensure the plunger 54 releases the connector 160 while a portion of the rod 156 extends from the actuator 154, thereby preventing the actuator from being damaged.

Figure 11:
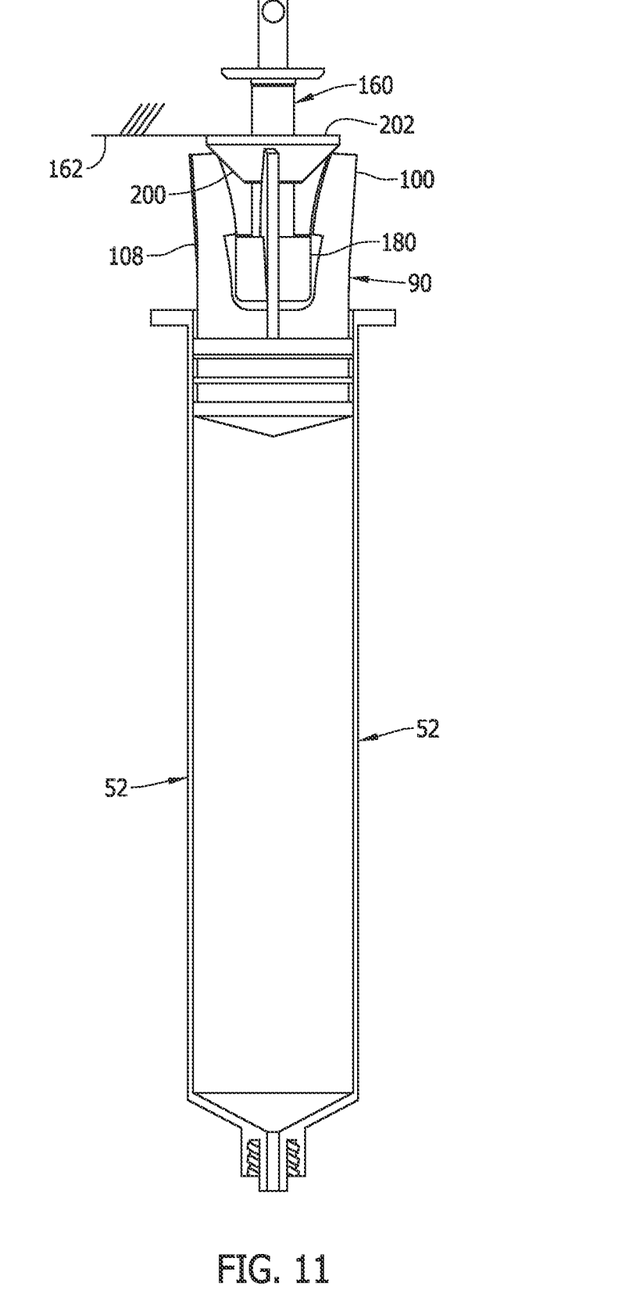
FIG. 11 is a front elevation of the syringe and the connector showing the spreader spreading the plunger blades to release the connector from the plunger.
Figure 13:
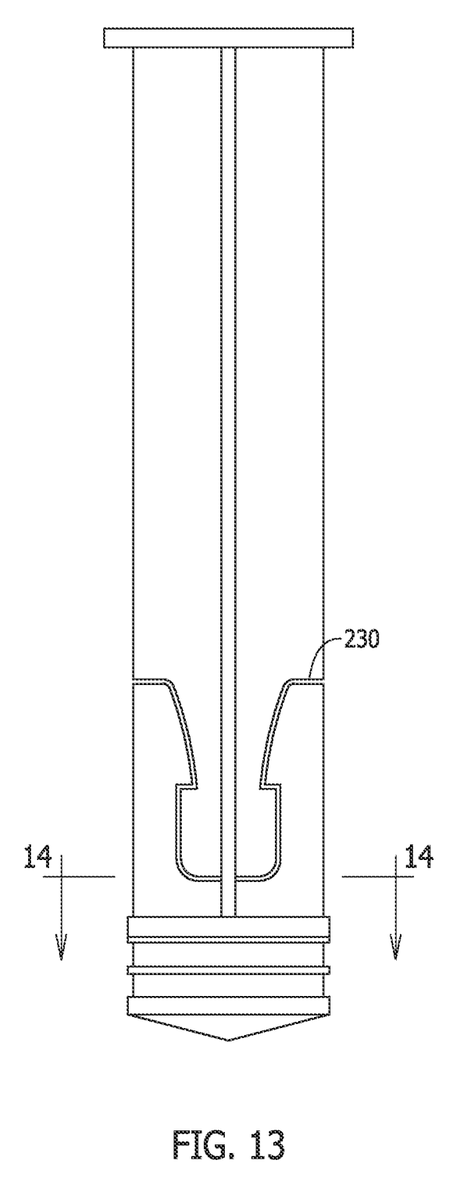
FIG. 13 is a front elevation of a plunger illustrating curfs made during a first cutting step of one method of manufacturing the plunger.
Figure 14:
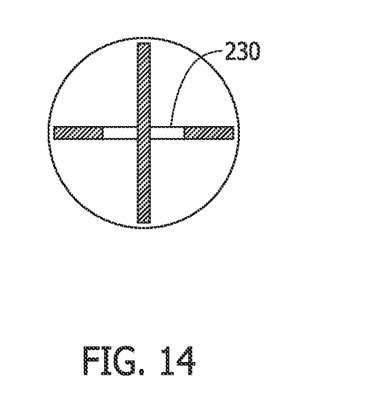
FIG. 14 is a cross section of the plunger taken in the plane of line 14-14 of FIG. 13.
Figure 15:
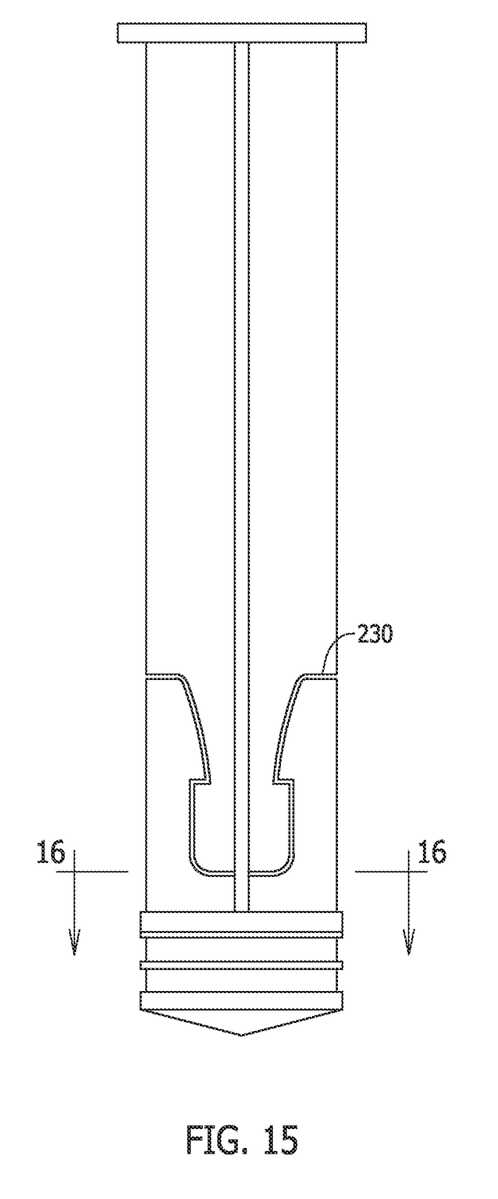
FIG. 15 is a front elevation of a plunger illustrating curfs made during a second cutting step of the method of manufacturing the plunger.
Figure 16:
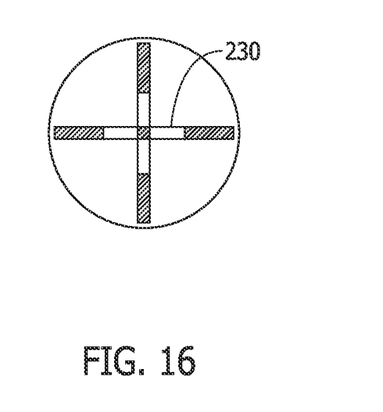
FIG. 16 is a cross section of the plunger taken in the plane of line 16-16 of FIG. 15.

The syringe 50 described above may be manufactured from a conventional syringe such as a 60 mL standard syringe available from Cardinal Health, Inc. of Dublin, Ohio. The plunger 54 and the barrel 52 are separated so the plunger can be modified as shown in FIGS. 11-14. The barrel 52 of the syringe is not modified. The conventional plunger 54 has an X-shaped cross section. First, the plunger 54 is mounted in a cutting fixture, and opposite blades of the plunger are partitioned, forming a curf 230 having a shape as shown in FIGS. 11 and 12. The plunger 54 is rotated ninety degrees about the longitudinal axis, positioned in the fixture, and the remaining blades of the plunger are partitioned, forming a curf 230 shaped as shown in FIGS. 13 and 14. The stem of the partitioned plunger is twisted to separate the central portion of the stem. The resulting plunger 54 has a configuration as described above. Those skilled in the art will appreciate that twisting the stem to shear the central portion of the stem results in a small projection at the center of the plunger receptacle 112. The projection need not be removed. A dimple may be formed in the connecting end of the fastener to accommodate the projection if desired.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

Having described the medical injector syringe and connector in detail, it will be apparent that modifications and variations are possible without departing from the scope of this description. Various changes in the above constructions, products, and methods are envisioned. Such changes are within the intended scope of this disclosure. Therefore, all matter contained in the above description and shown in the accompanying drawings shall be interpreted as illustrative and not in an overly limiting sense.

What is claimed is:

1. A syringe, comprising:
   a tubular syringe barrel having an interior surface defining a hollow interior of the barrel extending along a longitudinal axis between an open end and a closed end opposite said open end, said closed end having an orifice extending therethrough to a nozzle extending from the closed end of the syringe barrel opposite the hollow interior; and a syringe plunger, comprising:
- a support having a seal face and a connector face opposite said seal face; a seal attached to the seal face of the support, said seal being sized and shaped for sealing slidable engagement with the interior surface of the syringe barrel and defining a selectively variable volume hollow cavity within the interior of the syringe barrel between the seal and the closed end of the syringe barrel; and
- a receiver extending longitudinally from the connector face of the support, said receiver comprising a plurality of jaws spaced for receiving an injector fastener having an insertion end and a retention land spaced from the insertion end, each jaw of said plurality of jaws having an elastically deformable arm and a catching surface spaced from the connector face for engaging the retention land of the injector fastener when the injector fastener is seated between the jaws;
- wherein the arm of each jaw has an elongated cross-sectional shape including a thickness measured in a radial direction and a width measured transverse to the radial direction, said width being less than said thickness.

2. A syringe as set forth in claim 1, wherein each jaw extends from the support to a terminal end, said terminal end being spaced from the support by a distance greater than said thickness of the jaw.

3. A syringe as set forth in claim 2, wherein each jaw includes a sloping surface extending between the terminal end and the catching surface, said sloping surface being positioned closer to the longitudinal axis of the syringe barrel at the catching surface than at the terminal end of the jaw.

4. A syringe as set forth in claim 3, wherein said sloping surface includes a curved portion.

5. A syringe as set forth in claim 1, wherein each catching surface comprises an edge of the corresponding jaw.

6. A syringe as set forth in claim 5, wherein the edge of each jaw extends radially from an inner end to an outer end.

7. A syringe as set forth in claim 1, wherein the nozzle comprises a luer lock tip.

8. A syringe plunger for use in combination with a syringe barrel to dispense liquid, said syringe plunger comprising:
- a support having a seal face and a connector face opposite said seal face;
- a seal attached to the seal face of the support, said seal being sized and shaped for sealing slidable engagement with an interior surface of the syringe barrel and defining a selectively variable volume hollow cavity within an interior of the syringe barrel between the seal and a closed end of the syringe barrel; and
- a receiver extending longitudinally from the connector face of the support, said receiver comprising a plurality of jaws spaced for receiving an injector fastener having an insertion end and a retention land spaced from the insertion end, each jaw of said plurality of jaws having an elastically deformable arm and a catch spaced from the connector face for engaging the retention land of the injector fastener when the injector fastener is seated between the jaws;
- wherein the arm of each jaw has an elongated cross-sectional shape including a thickness measured in a radial direction and a width measured transverse to the radial direction, said width being less than said thickness.

9. A syringe plunger as set forth in claim 8, wherein each jaw extends from the support to a terminal end, said terminal end being spaced from the support by a distance greater than said thickness of the jaw.

10. A syringe plunger as set forth in claim 9, wherein each jaw includes a sloping surface extending between the terminal end and the catch, said sloping surface being positioned closer to the longitudinal axis of the syringe barrel at the catch than at the terminal end of the jaw.

11. A syringe plunger as set forth in claim 10, wherein said sloping surface includes a curved portion.

12. A syringe plunger as set forth in claim 8, wherein each catch comprises an edge of the corresponding jaw.

13. A syringe plunger as set forth in claim 12, wherein the edge of each jaw extends radially from an inner end to an outer end.

* * * * *